United States Patent [19]

Ahle

[11] Patent Number: 4,528,023
[45] Date of Patent: Jul. 9, 1985

[54] ENHANCEMENT OF HERBICIDAL ACTIVITY OF TETRAALUMINUM SALTS OF N-PHOSPHONOMETHYLGLYCINE

[75] Inventor: James L. Ahle, San Jose, Calif.

[73] Assignee: Stauffer Chemical Company, Westport, Conn.

[21] Appl. No.: 517,147

[22] Filed: Jul. 25, 1983

[51] Int. Cl.³ .............................................. A01N 25/30
[52] U.S. Cl. ..................................... 71/86; 71/DIG. 1
[58] Field of Search ............................... 71/86, DIG. 1

[56] References Cited

U.S. PATENT DOCUMENTS

| | | | |
|---|---|---|---|
| 3,455,675 | 7/1969 | Irani | 71/86 |
| 3,850,608 | 11/1974 | Hamm | 71/76 |
| 3,929,450 | 12/1975 | Hamm et al. | 71/86 |
| 4,341,549 | 7/1982 | Large et al. | 71/86 |
| 4,384,880 | 5/1983 | Large | 71/87 |
| 4,481,026 | 11/1984 | Prisbylla | 71/86 |

OTHER PUBLICATIONS

Kilhurry et al., (U.S. Pat. 4,043,752), Chem. Abst., vol. 87, (1977), 203061q.

Primary Examiner—Catherine L. Mills
Attorney, Agent, or Firm—Paul R. Martin

[57] ABSTRACT

A herbicidal composition comprising
(a) a herbicidally effective amount of a tetraaluminum salt of N-phosphonomethylglycine; and
(b) from 0.5 to 50% by weight polyethoxylated amine surfactant of the formula

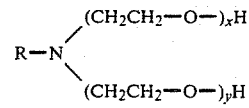

where R is tallow oil having an average of 18 carbon atoms and $x+y$ total 15.

8 Claims, No Drawings

ENHANCEMENT OF HERBICIDAL ACTIVITY OF TETRAALUMINUM SALTS OF N-PHOSPHONOMETHYLGLYCINE

BACKGROUND OF THE INVENTION

This invention relates to a herbicidal composition containing a tetraaluminum salt of N-phosphonomethylglycine which has enhanced herbicidal activity by virtue of the inclusion in the herbicidal composition of a polyethoxylated tallow amine.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are normally incorporated into the soil or surface applied prior to the emergence of the weed plants from the soil, and the post-emergence herbicides are normally applied to the plant's foliage after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides and contaminants were long lasting and were not readily biodegradable. While there has been some dispute between governmental agencies and commercial interests regarding the effects of residual products of 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. N-Phosphonomethylglycine and certain agriculturally effective salts have been approved for use by the U.S. Government, and, as a consequence, this herbicide has become extremely successful commercially.

THE PRIOR ART

N-Phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Other methods include the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. Nos. 3,868,407, 4,197,254, and 4,199,354, among others.

Specific salts of N-phosphonomethylglycine which have been disclosed to be herbicidally effective are the sulfonium and sulfoxonium salts.

Other salts are constantly being sought which are more economically and agriculturally efficient or cost effective than those previously known, or are easier to produce.

It has been found that certain metal salts, particularly the tetraaluminum salt of N-phosphonomethylglycine, is an effective herbicide, however, such salts have low solubility properties in water and thus their herbicidal activity is substantially limited as a consequence of this.

A reason for this has to do with the way that herbicidal compositions are applied by the farmer in the field. For shipping purposes, herbicidal compositions are formulated into dusts, wettable powders, granular pellets, concentrated emulsions and encapsulated granules. Once the herbicide is purchase by the farmer and carried out to the field, the farmer then normally will prepare an aqueous solution of the herbicide, and apply same to the soil or undesired plants by means of a spraying device.

The solution which he prepares is normally an aqueous one where the herbicide is dissolved, dispersed or emulsified in the water for spraying purposes. Obviously, if the post-emergent herbicide does not dissolve or disperse well in water, it will not penetrate the plants' leaves and will not be taken into the system, and the herbicidal activity will be diminished. The tetraaluminum salt of N-phosphonomethylglycine, is practicaly insoluble in water and organic solvents, and thus cannot be effectively applied in an effective manner to the locus where it is desired to have control.

DESCRIPTION OF THE INVENTION

It has now been discovered, however, that the herbicidal activity of the tetraaluminum salt of N-phosphonomethylglycine can be substantially improved by incorporating into the composition, from 0.05 to 50% by weight of a polyethoxylated tallow amine surfactant having the formula

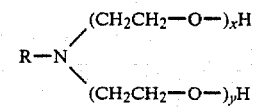

where R is tallow oil having an average of 18 carbon atoms and $x+y$ total 15.

The polyethoxylated tallow amine surfactant can be incorporated into the herbicide composition as a single component, however it is normally shipped by the manufacturer thereof as a solution of the surfactant in a solvent such a butanol or isopropanol. Accordingly, therefore, the preferred compositions of this invention comprise the tetraaluminum salt of N-phosphonomethylglycine, the polyethoxylated tallow amine surfactant, and an organic solvent.

Preferably, the solvent is present in an amount not exceeding 50% of the weight of the herbicide composition, and most preferably in an amount ranging from about 10 to about 50%.

In the preferred compositions, the weight ratio of herbicide to surfactant is about 2 parts herbicide to 1 part surfactant.

Representative formulations of the compositions of this invention are as follows:

| | |
|---|---|
| 10% | tetra-N—phosphonomethylglycine aluminum salt |
| 5% | Frigate ® (a solution of 70% polyethoxylated tallow amine and 30% butanol) |
| 85% | water |
| Total 100% | |
| 10% | tetra-N—phosphonomethylglycine aluminum salt |
| 5% | Ethomeen C/25 ® (a solution of 75% polyethoxylated tallow amine and 25% isopropanol) |
| 85% | Water |
| Total 100% | |

It is not known exactly how the polyethoxylated tallow amine works to enhance the herbicidal activity of the tetraaluminum salts of N-phosphonomethylglycine. However, it is believed that with increased solubility, the active herbicide is able to penetrate plant surfaces to a substantially greater extent that had been the case previously.

Practically any organic solvent can be used as a part of the composition. Suitable solvents include butanol, dimethylformamide, etc.

The compositions of this invention are made by simply mixing the herbicide with the organic solvent and the surfactant in any suitable container. Normally, the surfactant and solvent will come as a solution from the manufacturer.

The tetraaluminum salt of phosphonomethylglycine can be produced by reacting N-phosphonomethylglycine with aluminum in the presence of water in accordance with the method described in co-pending application Ser. No. 442,067, filed Nov. 16, 1982, now abandoned.

The preferred polyethoxylated tallow amine is sold by the Diamond Shamrock Corporation, Dallas, Tex., under the trade name Frigate ®. This is a mixture of 70% amine in 30% butanol. Similar compounds are sold under the trade names Ethomeen C/25 ® by Armak Industries, Chemical Division, Chicago, Ill.

The enhanced herbicidal activity of the compounds of the invention is exhibited by means of tests in accordance with the following procedure.

EXAMPLE 1

Herbicidal Activity Tests

This example offers herbicidal activity test data to show the effectiveness of the tetraaluminum salt of N-phosphonomethylglycine composition containing the polyethoxylated amine enhancer. The effect is observed by comparing the extent of weed control in test containers treated with the salt plus enhancer against that occuring in similar control containers treated with the salt alone. The soil used in these tests was a sandy loam soil from the Livermore, California area.

Also added to the soil was 17-17-17 fertilizer (N-$P_2O_5$-$K_2O$ on a weight basis), amounting to 50 ppm by weight with respect to the soil, and CAPTAN, a soil fungicide.

The treated soil was then placed in plastic tubs, 6 inches in diameter and 5 inches deep with drainage holes. Johnsongrass rhizomes, Bermuda grass cuttings, and purple nutsedge tubers were planted. The test weeds were as follows:

| COMMON NAME | SCIENTIFIC NAME |
|---|---|
| Grasses: | |
| A. johnson grass | *Sorghum halepense* |
| B. bermuda grass | *Cynodon dactylon* |
| C. purple nutsedge | *Cyperus rotundus* |

Sufficient stock or cuttings were planted to produce several seedlings per tub. After planting, the tubs were then placed in a greenhouse maintained at 70° to 85° F. (21° to 30° C.) and watered daily by sprinkler.

Chemical application was made by spraying approximately 35 days after planting.

The spray solution for Composition No. 1 in Table I below is prepared by mixing 0.4 g of the tetraaluminum salt of N-phosphonomethylglycine with 39.4 g of a 50-50 acetone-water mixture plus 0.2 g Tween ® 20 (polyoxyethylene sorbitan monolaurate).

The spray solution for Composition No. 2 in Table I below is prepared by dissolving 0.4 g of the tetraaluminum salt of N-phosphonomethylglycine plus 39.4 g of water and adding thereto 0.2 g Frigate ®.

Twenty grams (20 g) of this solution is added to 20 g of $H_2O$ and sprayed at 25 gallon/acre, resulting in a 1.0 lb/acre rate of chemical application. Other rates were achieved by varying the solution concentration.

Approximately 28 days after treatment, the degree of weed control was estimated and recorded as percentage control compared to the growth of the same species in an untreated check tubs of the same age. The rating scale ranges from 0 to 100%, where 0 equals no effect with plant growth equal to the untreated control, and 100 equals complete kill.

The results are listed in Table I below. It is clear that the compositions of this invention have enhanced activity as a consequence of the addition thereto of the polyethoxylated amines described herein.

TABLE I

| | | HERBICIDE TEST RESULTS | | | | | | | | |
|---|---|---|---|---|---|---|---|---|---|---|
| | | Percent Control | | | | | | | | |
| | Appln. | Johnsongrass | | | Bermuda grass | | | Purple nutsedge | | |
| Comp. No. | Rate (lb/A) | Rep. 1 A | Rep. 2 A | Ave | Rep. 1 B | Rep. 2 B | Ave | Rep. 1 C | Rep. 2 C | Ave |
| 1 | 0.25 | 0 | 20 | 10 | 0 | 0 | 0 | — | — | — |
| (con- | 0.50 | 60 | 81 | 70 | 40 | 40 | 40 | 0 | 10 | 5 |
| trol) | 1.00 | — | — | — | — | — | — | 40 | 50 | 45 |
| 2 | 0.25 | 90 | 100 | 95 | 80 | 80 | 80 | — | — | — |
| | 0.50 | 100 | 100 | 100 | 95 | 95 | 95 | 80 | 80 | 80 |
| | 1.00 | — | — | — | — | — | — | 95 | 98 | 97 |

Ave = Average of two replications.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. Post-emergence foliar application is preferred. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of emulsifiable or liquid concentrates.

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 20 weight percent of the total composition.

Thus, emulsifiable or liquid concentrates of the present invention will consist of from about 10 to about 50 weight percent active material, about 40 to 85 weight percent solvent, and about 1 to 20 weight percent emulsifier. Other additives such as spreading agents and stickers can also be included.

IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Foliar application is preferred. Liquid compositions can be applied by the use of boom and hand sprayers. The compositions can also be applied from airplanes sprays because they are effective in very low dosages.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A herbicidal composition comprising
   (a) a herbicidally effective amount of a tetraaluminum salt of N-phosphonomethylglycine; and
   (b) from 0.5 to 50% by weight polyethoxylated amine surfactant of the formula

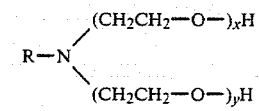

where R is tallow oil having an average of 18 carbon atoms and $x+y$ total 15.

2. The composition of claim 1 which additionally contains from 0 to 50% by weight organic solvent.

3. The composition of claim 1 in which the solvent is selected from butanol, isopropyl alcohol and dimethylformamide.

4. The composition of claim 3 in which the solvent is butanol.

5. A method for controlling weeds which comprises applying to the locus where control is desired, a herbicidally effective amount of a composition comprising:
   (a) a herbicidally effective amount of a tetraaluminum salt of N-phosphonomethylglycine; and
   (b) from 0.5 to 50% by weight polyethoxylated amine surfactant of the formula

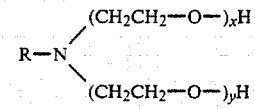

where R is tallow oil having an average of 18 carbon atoms and $x+y$ total 15.

6. The method of claim 5 in which the composition additionally contains from 0 to 50% organic solvent.

7. The method of claim 6 in which the organic solvent is butanol.

8. The method of claim 6 in which the surfactant is polyethoxylated tallow amine.

* * * * *